US011247007B2

(12) United States Patent
Nitta et al.

(10) Patent No.: US 11,247,007 B2
(45) Date of Patent: Feb. 15, 2022

(54) SILENCER AND ARTIFICIAL VENTILATOR

(71) Applicant: Metran Co., Ltd., Kawaguchi (JP)

(72) Inventors: Kazufuku Nitta, Saitama (JP); Shinichi Shiota, Saitama (JP)

(73) Assignee: Metran Co., Ltd., Kawaguchi (JP)

( * ) Notice: Subject to any disclaimer, the term of this patent is extended or adjusted under 35 U.S.C. 154(b) by 229 days.

(21) Appl. No.: 15/767,402

(22) PCT Filed: Sep. 16, 2016

(86) PCT No.: PCT/JP2016/077361
§ 371 (c)(1),
(2) Date: Apr. 11, 2018

(87) PCT Pub. No.: WO2017/064975
PCT Pub. Date: Apr. 20, 2017

(65) Prior Publication Data
US 2018/0280643 A1 Oct. 4, 2018

(30) Foreign Application Priority Data
Oct. 16, 2015 (JP) .............................. JP2015-205055

(51) Int. Cl.
*A61M 16/00* (2006.01)
*A61M 16/16* (2006.01)
*F04D 25/08* (2006.01)
(52) U.S. Cl.
CPC .......... *A61M 16/022* (2017.08); *A61M 16/16* (2013.01); *A61M 16/0066* (2013.01); *A61M 2205/42* (2013.01); *F04D 25/08* (2013.01)
(58) Field of Classification Search
CPC ................ A61M 16/022; A61M 16/16; A61M 2205/42; A61M 16/0066; F04D 29/663; F04D 29/664; F04D 29/665
See application file for complete search history.

(56) References Cited

U.S. PATENT DOCUMENTS

| 4,367,734 A * | 1/1983 | Benthin | A61M 16/16 |
| | | | 128/204.13 |
| 4,381,267 A * | 4/1983 | Jackson | A61M 16/16 |
| | | | 128/204.13 |

(Continued)

FOREIGN PATENT DOCUMENTS

| JP | 2006-223332 A | 8/2006 |
| JP | 2014-508594 A | 4/2014 |

(Continued)

OTHER PUBLICATIONS

International Search Report, with English translation, and Written Opinion issued in PCT/JP2016/077361 dated Dec. 20, 2016 (8 pages).

(Continued)

*Primary Examiner* — Joseph D. Boecker
*Assistant Examiner* — Brian T Khong
(74) *Attorney, Agent, or Firm* — Flynn Thiel, P.C.

(57) ABSTRACT

A silencer having improved ease of maintenance and a small size and light weight and a respiratory assistance device. The silencer is provided to therapy equipment where pressurized air is generated by a blower, and the pressurized air is supplied to an airway of a patient from an attachment part attached to the patient, the silencer being inserted into a flow passage so as to reduce sound generated by the therapy equipment, the pressurized air being introduced from the blower to the patient through the flow passage. The silencer is provided outside a casing which accommodates the blower.

3 Claims, 6 Drawing Sheets

(56) References Cited

U.S. PATENT DOCUMENTS

| | | | | |
|---|---|---|---|---|
| 4,905,789 A * | 3/1990 | Francis | ............ | A61M 16/0057 181/224 |
| 5,647,344 A * | 7/1997 | Turnbull | ............ | A61M 16/1045 128/201.13 |
| 5,821,473 A * | 10/1998 | Takahashi | ............ | F04D 29/664 181/224 |
| 5,841,080 A * | 11/1998 | Iida | ............ | F01N 1/24 181/225 |
| 6,367,472 B1 * | 4/2002 | Koch | ............ | A61M 16/1075 128/203.12 |
| 7,428,902 B2 * | 9/2008 | Du | ............ | A61M 16/1045 128/200.24 |
| 7,458,615 B2 * | 12/2008 | White | ............ | A61M 16/08 285/272 |
| 7,708,013 B2 * | 5/2010 | Niland | ............ | B01F 5/0476 128/201.13 |
| 7,938,113 B2 * | 5/2011 | Weinstein | ............ | A61M 16/026 128/203.26 |
| 9,375,546 B2 * | 6/2016 | Ruff | ............ | A61M 16/1045 |
| 10,398,871 B2 * | 9/2019 | Cortez, Jr | ............ | A61M 16/142 |
| 2002/0134378 A1 * | 9/2002 | Finnegan | ............ | A61M 16/00 128/200.24 |
| 2004/0065335 A1 * | 4/2004 | Huber | ............ | A61M 16/1075 128/206.21 |
| 2004/0231913 A1 * | 11/2004 | McCombs | ............ | B01D 39/083 181/258 |
| 2007/0277825 A1 * | 12/2007 | Bordewick | ............ | A61M 16/0683 128/204.23 |
| 2008/0127976 A1 * | 6/2008 | Acker | ............ | A61M 16/0627 128/204.18 |
| 2008/0257346 A1 * | 10/2008 | Lathrop | ............ | A61M 16/0066 128/204.17 |
| 2009/0126735 A1 | 5/2009 | Nitta | | |
| 2010/0006097 A1 * | 1/2010 | Frater | ............ | A61M 16/0057 128/204.18 |
| 2011/0200426 A1 * | 8/2011 | Takano | ............ | F04D 29/4226 415/119 |
| 2012/0145155 A1 * | 6/2012 | Peake | ............ | A61M 16/0816 128/205.12 |
| 2012/0157794 A1 * | 6/2012 | Goodwin | ............ | A61B 5/0826 600/301 |
| 2013/0263854 A1 * | 10/2013 | Taylor | ............ | A61M 16/0816 128/204.23 |
| 2013/0306072 A1 | 11/2013 | Moir et al. | | |
| 2015/0003966 A1 * | 1/2015 | Duquette | ............ | F04D 17/10 415/119 |
| 2015/0219119 A1 | 8/2015 | Nitta et al. | | |
| 2015/0320954 A1 * | 11/2015 | Suzuki | ............ | A61M 16/0066 128/204.21 |
| 2016/0184539 A1 * | 6/2016 | Suzuki | ............ | A61M 16/0066 128/205.25 |
| 2016/0193437 A1 * | 7/2016 | Bao | ............ | G16H 40/63 128/203.14 |

FOREIGN PATENT DOCUMENTS

| | | |
|---|---|---|
| JP | 2014-132156 A | 7/2014 |
| WO | WO 2015/019574 A1 | 2/2015 |

OTHER PUBLICATIONS

Search Report of European Patent Office issued in European Applicaiton No. 16 85 5229 dated Oct. 25, 2018 (4 pages).

* cited by examiner

US 11,247,007 B2

SILENCER AND ARTIFICIAL VENTILATOR

TECHNICAL FIELD

The present invention relates to a silencer and an artificial ventilator to which the silencer is connected.

BACKGROUND ART

Conventionally, artificial ventilators have been used for patients suffering from respiratory failure due to various pathological conditions. For the artificial ventilators, a respiratory assistance device for CPAP (Continuous positive airway pressure) therapy is generally known which is used for treatment of Sleep Apnea Syndrome (SAS). SAS occurs in such a manner that muscles of the airway relax during sleep so that the root of the tongue or the soft palate lowers thus obstructing the airway. It is said that the number of potential SAS patients in Japan is more than three million. The risk of occurrence of circulatory system disease for an SAS patient is considered two to four times higher than for a healthy person. Further, an SAS patient has a high possibility of having sleeping disorders which cause the patient to exhibit symptoms of severe drowsiness and hence, the risk of occurrence of a traffic accident for an SAS patient is two or more times higher than for a healthy person. It is considered effective for a patient suffering from SAS to receive Continuous Positive Airway Pressure therapy (CPAP therapy) which utilizes a respiratory assistance device including a blower which applies a positive pressure to the airway. Such a respiratory assistance device uses compressed air supplied from the blower as intake air, and supplies the pressurized air to the airway of a patient.

A respiratory assistance device used for CPAP therapy requires a high flow rate so that a blower and an attachment part which supplies pressurized air to the nose portion and the like are connected to each other by a relatively wide air tube (corrugated tube) having a diameter of 15 mm to 22 mm. During CPAP therapy, a positive pressure of approximately 4.0 to 20.0 cm $H_2O$ is applied. The respiratory assistance device includes the blower so as to generate pressurized air. A rotational speed of an impeller of the blower reaches 10000 to 20000 rpm. Accordingly, without any innovation, airflow noise of the impeller or vibrations of a motor reaches the attachment part on the patient through the air tube which introduces pressurized air therethrough thus causing sleep disturbance.

FIG. 5 shows the configuration of a conventional respiratory assistance device 80. The respiratory assistance device includes a casing 85, a humidifier 40, an air tube 60, and an attachment part 70. The casing 85 has a substantially sealed structure so as to attenuate sound. The casing 85 includes a control part 10, a blower 20, a silencer 30, and a flow passage 50. The blower 20 is disposed in a silencer box 90 accommodated in a casing of the respiratory assistance device. With such a configuration, noises from the blower 20 can be reduced. A preliminary effort to reduce sound generated by the blower 20 has been also made (see Japanese Patent Laid-Open No. 2014-132156, for example).

SUMMARY OF INVENTION

Technical Problem

However, a porous material, for example, urethane foam or the like, which is used for forming a silencing member of the silencer 30 is constantly exposed to vibrations and hence, the silencing member is easily deteriorated. Further, sound attenuation performance of silencing member is lowered along with the deterioration of the silencing member. The porous structure adopted for absorbing sound easily absorbs moisture from the humidifier 40 and hence, bacteria easily proliferate thus causing many sanitary problems.

The present invention has been made under such circumstances, and it is an object of the present invention to provide a silencer having improved ease of maintenance and a small size and light weight and a respiratory assistance device.

Solution to Problem (1) The present invention provides a silencer provided to therapy equipment where pressurized air is generated by a blower, and the pressurized air is supplied to an airway of a patient from an attachment part attached to the patient, the silencer being inserted into a flow passage so as to reduce sound generated by the therapy equipment, the pressurized air being introduced from the blower to the patient through the flow passage, wherein the silencer is provided outside a casing which accommodates the blower.

(2) The present invention provides the silencer described in the above-mentioned (1), and characterized in that the silencer is freely insertable into the flow passage.

(3) The present invention provides the silencer described in the above-mentioned (1) or (2), and characterized in that the silencer has a humidifier connection portion for connecting the silencer to a humidifier configured to humidify the pressurized air.

(4) The present invention provides the silencer described in the above-mentioned (3), and characterized in that the humidifier includes: a water storage part configured to store water for humidification; and a humidifying part configured to humidify the pressurized air.

(5) The present invention provides the silencer described in the above-mentioned (4), and characterized in that the humidifying part includes: a porous hollow fiber; a water introduction passage through which water is introduced from the water storage part to the hollow fiber; and a connector configured to detachably connect the water introduction passage and the hollow fiber to each other.

(6) The present invention provides the silencer described in any one of the above-mentioned (1) to (5), and characterized in that the silencer includes: a housing part having an inner space; a first connection portion connectable to the flow passage on a side of the blower configured to provide the pressurized air; and a second connection portion connectable to the flow passage on a side of the attachment part.

(7) The present invention provides the silencer described in the above-mentioned (6), and characterized in that the housing part has a silencing member in the inner space, and the silencing member is disposed between the first connection portion and the second connection portion in the inner space of the housing part, and has at least one through hole portion through which the pressurized air is introduced from the blower side to the attachment part side.

(8) The present invention provides the silencer described in the above-mentioned (6), and characterized in that the housing part has a filter in the inner space, and the filter is disposed between the first connection portion and the second connection portion in the inner space of the housing part.

(9) The present invention provides the silencer described in any one of the above-mentioned (6) to (8), and characterized in that the first connection portion has a female portion which has an inner diameter equal to an outer diameter of an end portion of an air tube through which the pressurized air is introduced to the attachment part, the female portion being directly connectable to a breathing circuit connection port of a casing which accommodates the blower, and the second connection portion has a male portion which has an outer diameter equal to an inner diameter of the end portion of the air tube, the male portion being connectable to the air tube.

(10) The present invention provides the silencer described in any one of the above-mentioned (6) to (8), and characterized in that the first connection portion has a male portion which has an outer diameter equal to an inner diameter of an end portion of an air tube through which the pressurized air is introduced to the attachment part, the male portion being connectable to the air tube, and the second connection portion has a male portion which has an outer diameter equal to the inner diameter of the end portion of the air tube, the male portion being connectable to the air tube.

(11) The present invention provides the silencer described in any one of the above-mentioned (6) to (10), and characterized in that the housing part is separable into a first housing member having the first connection portion, and a second housing member having the second connection portion.

(12) The present invention provides the silencer described in any one of the above-mentioned (3) to (5), and characterized in that the silencer includes: a housing part having an inner space; a first connection portion connectable to the flow passage on a side of the blower configured to provide the pressurized air; and a second connection portion connectable to the flow passage on a side of the attachment part, the housing part is separable into a first housing member having the first connection portion, and a second housing member having the second connection portion, and the humidifier connection portion is provided to the second housing member.

(13) The present invention provides the silencer described in the above-mentioned (12), and characterized in that the housing part has a silencing member in the inner space, and the silencing member is disposed between the first connection portion and the second connection portion in the inner space of the housing part, and has at least one through hole portion through which the pressurized air is introduced from the blower side to the attachment part side.

(14) The present invention provides the silencer described in the above-mentioned (12), and characterized in that the housing part has a filter in the inner space, and the filter is disposed between the first connection portion and the second connection portion in the inner space of the housing part.

(15) The present invention provides the silencer described in any one of the above-mentioned (6) to (14), and characterized in that a cross-sectional area of the inner space of the housing part taken along a plane direction perpendicular to the flow passage is larger than a cross-sectional area of the first connection portion taken along a plane direction perpendicular to the flow passage.

(16) The present invention provides an artificial ventilator characterized by including the silencer described in any one of the above-mentioned (1) to (15).

Advantageous Effect of Invention

According to the present invention, the silencer is disposed outside the casing which accommodates the blower generating pressurized air and hence, it is possible to acquire an advantageous effect of enhancing ease of maintenance of the silencer.

DESCRIPTION OF EMBODIMENTS

Figure 1:
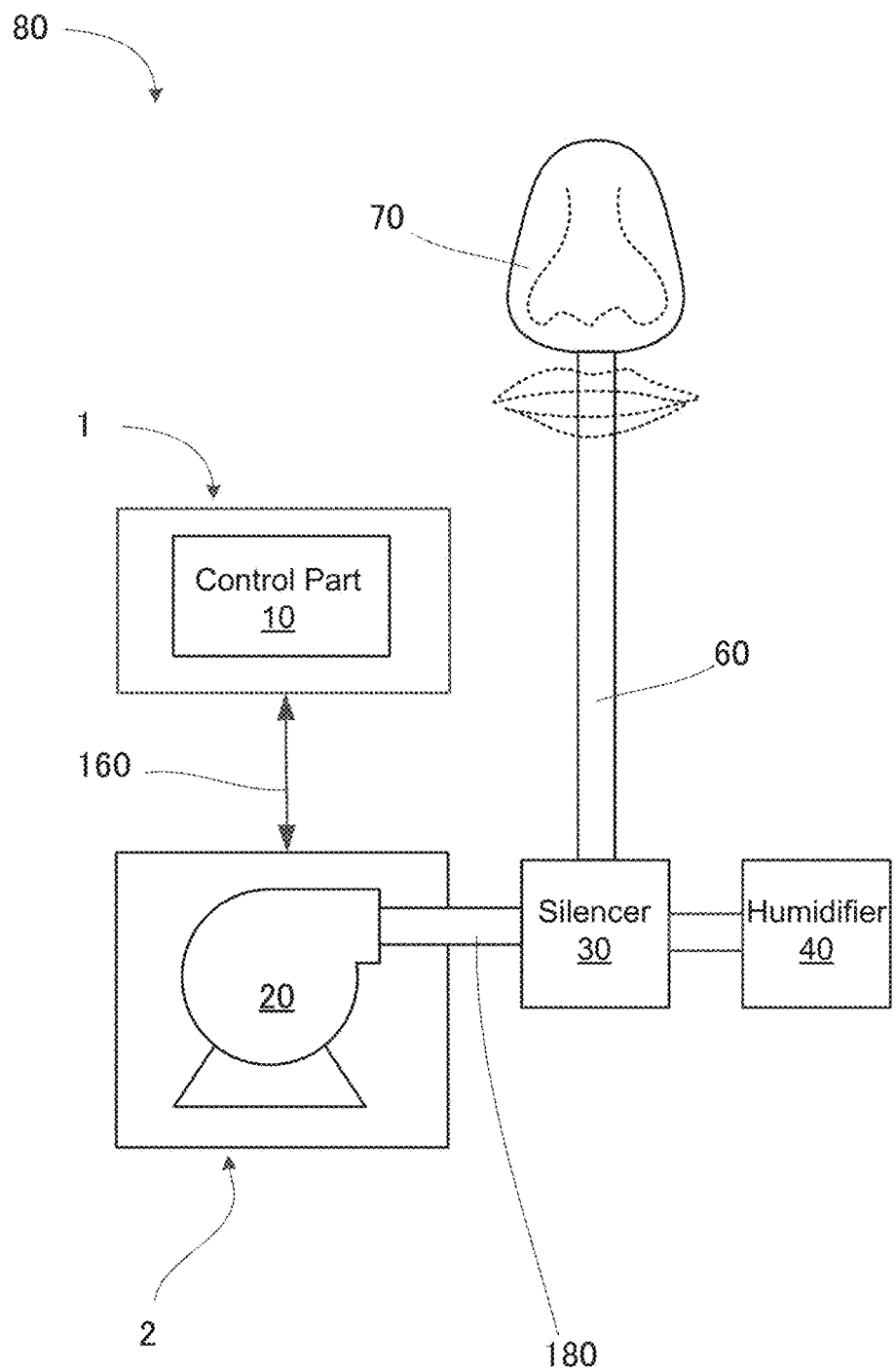
FIG. 1 is an explanatory view showing the configuration of a respiratory assistance device according to an embodiment of the present invention.
Figure 2:
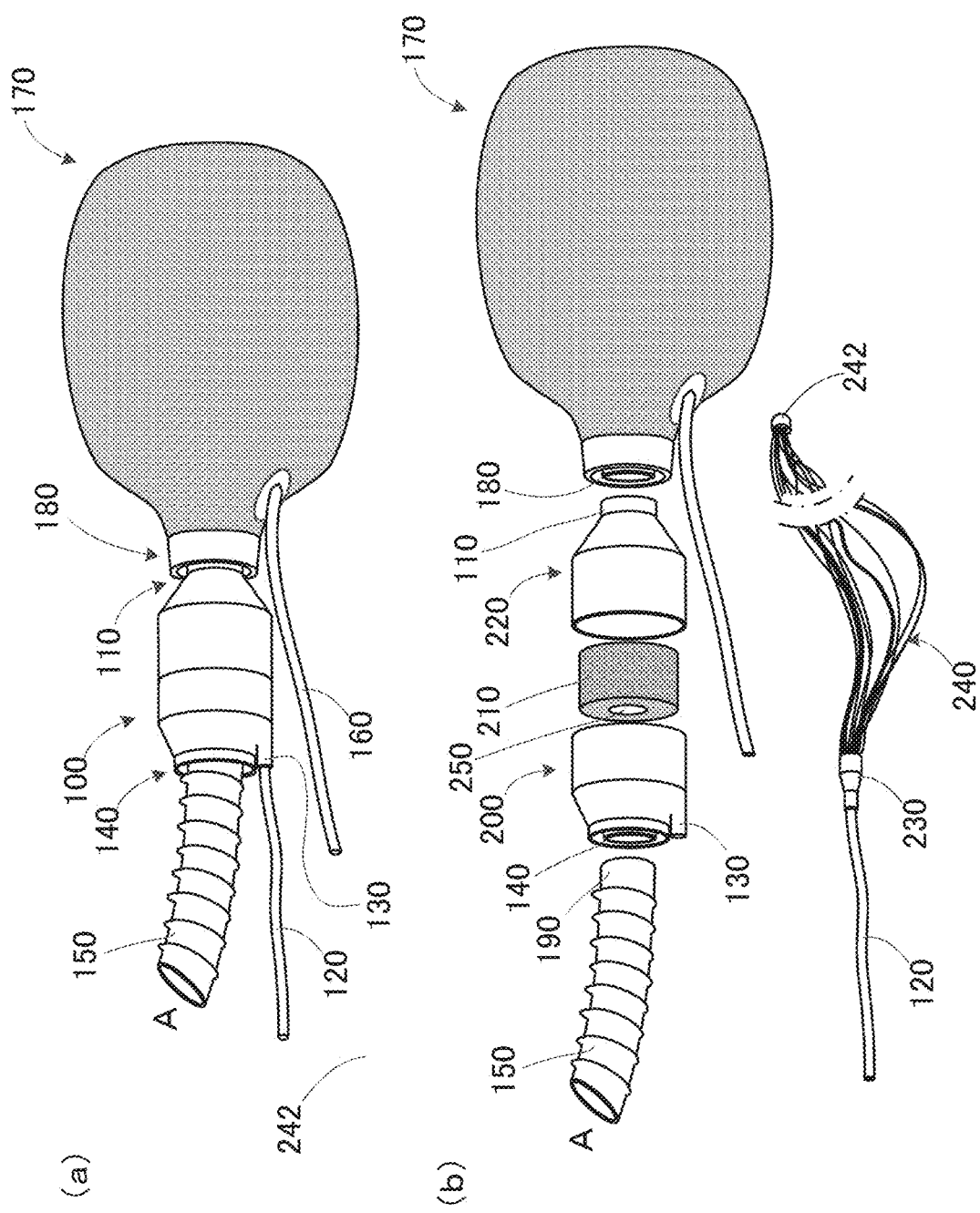
FIG. 2 is an explanatory view of a silencer of the respiratory assistance device.

Hereinafter, preferred embodiments of a silencer and a respiratory assistance device equipped with the silencer of the present invention are described in detail with reference to FIG. 1 to FIG. 5. FIG. 1 to FIG. 5 show only one example of a mode for carrying out the invention. In the drawings, parts given the same numerals indicate identical parts.

FIG. 1 shows the overall configuration of a respiratory assistance device (one kind of artificial ventilator) 80 according to a first embodiment of the present invention. The respiratory assistance device 80 as therapy equipment is formed of: a control device 1; a blower device 2; a silencer 30; a humidifier 40; an air tube 60; and an attachment part 70. The control device 1 includes a control part 10, and a blower 20 is disposed in the blower device 2. The control device 1 and the blower device 2 are connected to each other via an electric power distribution line and communication means 160. The control device 1 performs control based on information from pressure measuring means and flow rate measuring means (not shown in the drawing) disposed in the blower device 2, and performs the control such that the flow rate of the blower 20 assumes a value set in advance. Sound of pressurized air generated by the blower 20 is attenuated by the silencer 30 disposed outside the blower device 2, and connected to a breathing circuit connection port 180. The pressurized air is made to pass through the air tube 60, and is introduced into the airway of a patient from the attachment part 70. The humidifier 40 is connected to the silencer 30 so that the pressurized air is humidified whereby there is no possibility that the patient has the feeling of discomfort due to dry pressurized air. In this drawing and other drawings, sizes, shapes, thicknesses and the like of members are expressed in an exaggerated manner where necessary.

FIG. 2(a) is a view showing the overall configuration where the silencer 30 according to the first embodiment, the humidifier 40, and a blower device 170 are connected with each other.

The blower device 170 supplies pressurized air from the breathing circuit connection port 180. A first connection portion 110 of the silencer 100 is directly connected to the breathing circuit connection port 180. The silencer 100 has a second connection portion 140 on the side opposite to the first connection portion 110, and the second connection portion 140 is connected to an air tube 150. A portion A is connected to the attachment part 70 which covers the nose portion of the patient. The silencer 100 has a humidifier connection portion 130 to which the humidifier 40 is connected, and water is supplied to a humidifying part disposed in the silencer 100 through a water introduction passage 120 connected to the humidifier connection portion 130.

FIG. 2(b) is an exploded view of the silencer 30, the humidifier 40, and the blower device 170.

The silencer 100 is formed of a first housing member 220, a second housing member 200, and a silencing member 210. The first housing member 220 and the second housing member 200 are connected to each other by way of a connecting portion equipped with a packing so as to prevent leakage of pressurized air. The first housing member 220 and the second housing member 200 are separable from each other. A casing of the first housing member 220 and a casing of the second housing member 200 may be connected to each other such that male threads are formed on the casing of the first housing member 220 and female threads are formed on the casing of the second housing member 200.

Each of the first housing member 220 and the second housing member 200 has a hollow shape thus forming a housing part which can dispose the silencing member 210 therein. In this configuration, the silencing member 210 has a through hole portion 250 for introducing pressurized air from the first connection portion 110 to the second connection portion 140. With such a configuration, the silencing member 210 can be easily replaced and hence, ease of maintenance is improved. Further, compared to an area of the first connection portion 110 in cross section taken along the plane direction perpendicular to a flow passage and an area of the second connection portion 140 in cross section taken along the plane direction perpendicular to the flow passage, the first housing member 220 and the second housing member 200 respectively have a larger area in cross section taken along the plane direction perpendicular to the flow passage. Accordingly, the first housing member 220 and the second housing member 200 form an expansion type silencer which lowers density of energy of sound which passes through the first connection portion 110. Therefore, the silencing member 210 absorbs sound and, at the same time, it is possible to acquire an advantageous effect of attenuating sound. A cross-sectional area of the silencing member 210 in the plane direction perpendicular to the flow passage in the through hole portion 250 is small compared to the area of the first housing member 220 in cross section taken along the plane direction perpendicular to the flow passage. The cross-sectional area of the silencing member 210 is also small compared to the area of the second housing member 200 in cross section taken along the plane direction perpendicular to the flow passage. Accordingly, an expansion-type two-stage silencer is formed as a whole.

The first connection portion 110 of the first housing member 220 has a female portion which can be directly connected to the breathing circuit connection port 180 of the blower device 170. In this configuration, it is desirable that an inner diameter of the first connection portion 110 be substantially equal to an outer diameter of the breathing circuit connection port 180 so that when the first connection portion 110 is attached onto the breathing circuit connection port 180, the breathing circuit connection port 180 is fastened by the first connection portion 110 due to elasticity of the first connection portion 110 to an extent that leakage of pressurized air is prevented. The second connection portion 140 of the second housing member 200 has a male portion which can be connected to an air tube end portion 190. It is desirable that an inner diameter of the air tube 150 and an outer diameter of the second connection portion 140 be substantially equal to each other so that, when the air tube end portion 190 is attached onto the second connection portion 140, the second connection portion 140 is fastened by the air tube end portion 190 due to elasticity of the air tube to an extent that leakage of pressurized air is prevented.

The humidifier is connected to the humidifier connection portion 130 of the second housing member 200. The humidifier is mainly formed of the water introduction passage 120, a connector 230, a humidifying part 240, and a water storage part (not shown in the drawing). The water introduction passage 120 supplies water to the humidifying part 240 from the water storage part through the connector 230. The connector 230 detachably connects the water introduction passage 120 and the humidifying part 240 with each other. The humidifying part 240 is formed of a bundle of a large number of hollow fibers, and is disposed in the air tube 150. The hollow fiber is made of a porous material having fine pores allowing vapor moisture to pass therethrough but not allowing liquid water to pass therethrough. It is desired that a packing member be disposed between the humidifier connection portion 130 and the water introduction passage 120 thus providing sealing between the humidifier connection portion 130 and the water introduction passage 120 so as to prevent leakage of pressurized air. Moisture is evaporated in the air tube 150 through the fine pores in the hollow fibers so that pressurized air is humidified. An end surface of the humidifying part 240 on the side opposite to the connector 230 is closed by a cap 242 thus preventing water from leaking from end surfaces of the hollow fibers.

The water introduction passage 120 may be held by a portion of the second housing member 200 in the silencer 100. The humidifying part 240 is desirably removable from the connector 230 for the purpose of replacement. This is because the humidifying part 240 is porous, and contains moisture in many cases and hence, bacteria easily proliferate whereby it is desirable to regularly replace the humidifying part 240 so as to prevent the occurrence of a sanitary problem.

Figure 3:
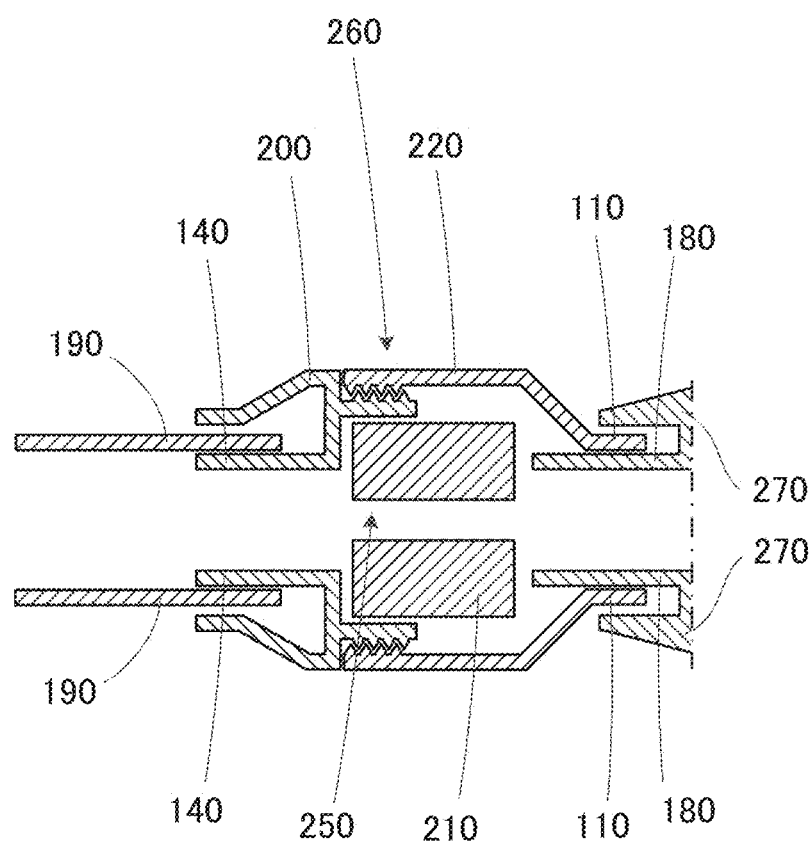
FIG. 3 is a cross-sectional view of a first embodiment of the silencer.

Next, the manner of operation of the silencer is described with reference to FIG. 3 which is a cross-sectional view of the silencer 30. In FIG. 3, the humidifier connection portion 130 is omitted. The silencer 30 is formed such that the first housing member 220 and the second housing member 200 are connected to each other via a housing member connection portion 260. The silencer 30 includes the silencing member 210 in a hollow housing part disposed inside thereof. Pressurized air enters the silencer 30 from a blower device casing end portion 270, and passes through the first connection portion 110 from the breathing circuit connection port 180 and, then, reaches the first housing member 220. The first housing member 220, the second housing member 200, and the silencing member 210 form an expansion-type two-stage silencer so that sound which enters silencer from the first connection portion 110 is attenuated by the silencer. After sound is attenuated, pressurized air is introduced into the air tube through the air tube end portion 190 from the second connection portion 140.

The detailed configuration of the silencer and the respiratory assistance device is further described.

Figure 4:
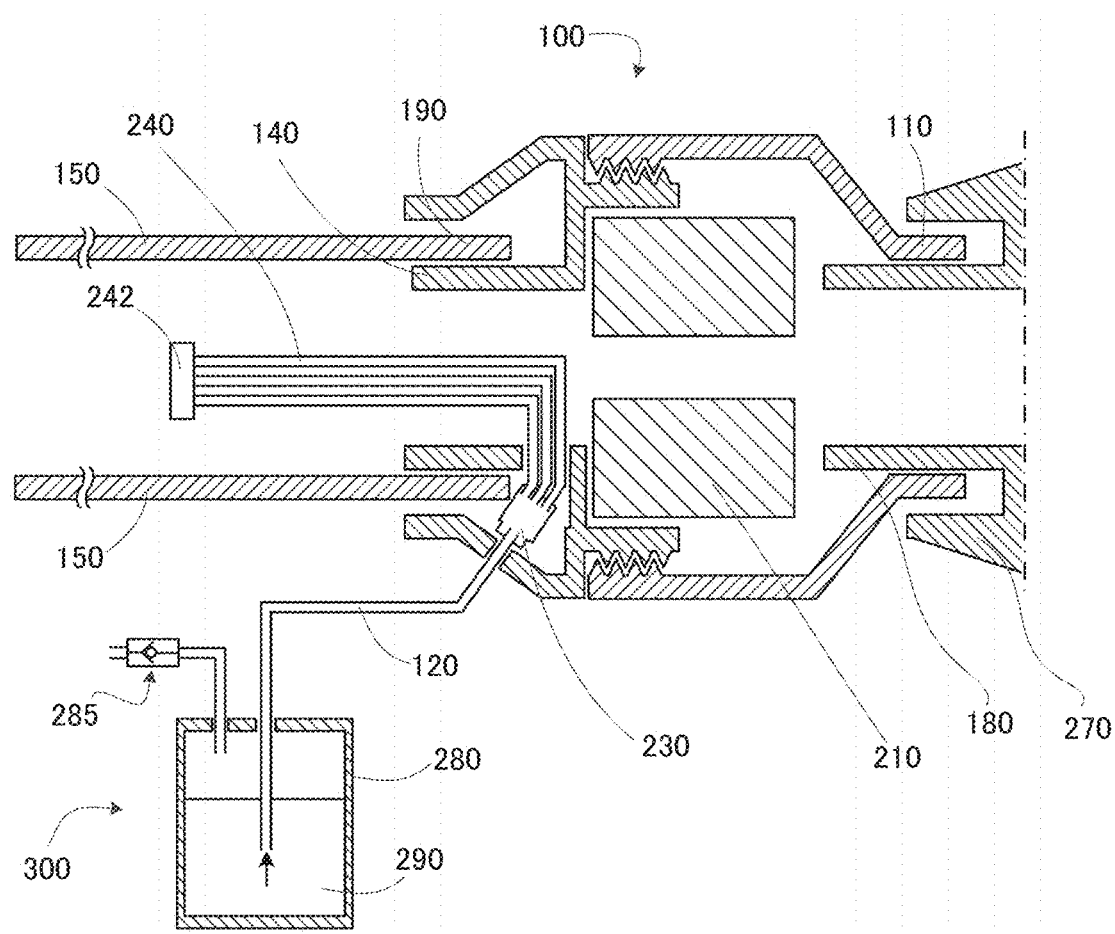
FIG. 4 is an explanatory view of the silencer and a humidifier connected to the silencer.

FIG. 4 is an explanatory view of the silencer 100 and the humidifier 300 connected to the silencer 100. The humidifier 300 is formed of a water storage part 280, the water introduction passage 120, the connector 230, and the humidifying part 240. The water storage part 280 is equipped with a check valve 285, and water 290 is stored in the water storage part. The water storage part 280 is formed of an elastic member so that the water storage part 280 can apply a pressure to the water 290 by being compressed by hand. The configuration is adopted due to the following reasons. It is necessary for pressurized air to be continuously humidified during sleep. When a pressure higher than a pressure in the air tube 150 is not applied to the water 290 in the water storage part 280, moisture is not easily evaporated from the humidifying part 240. Accordingly, it is necessary to constantly pressurize the water 290. When air in the water storage part 280 is not sufficient, air is injected into the water storage part 280 via the check valve 285. The humidifying part 240 is disposed in the air tube. Moisture is pressurized by the water storage part 280, and is introduced into the silencer 100 from the humidifier connection portion 130 through the water introduction passage 120. The moisture is evaporated from the porous hollow fibers forming the humidifying part 240 into the air tube 150 so as to perform humidification. Compared to conventional humidifiers of a heating type, that is, a type where moisture evaporated by heating a water storage part 280 is added to pressurized air so as to perform humidification, the humidifier 300 according to the present invention does not require a heater or a power source for heating thus having improved safety. Further, the humidifier 300 according to the present invention is of a natural evaporation type and hence, there is no possibility that pressurized air is excessively heated.

Figure 5:
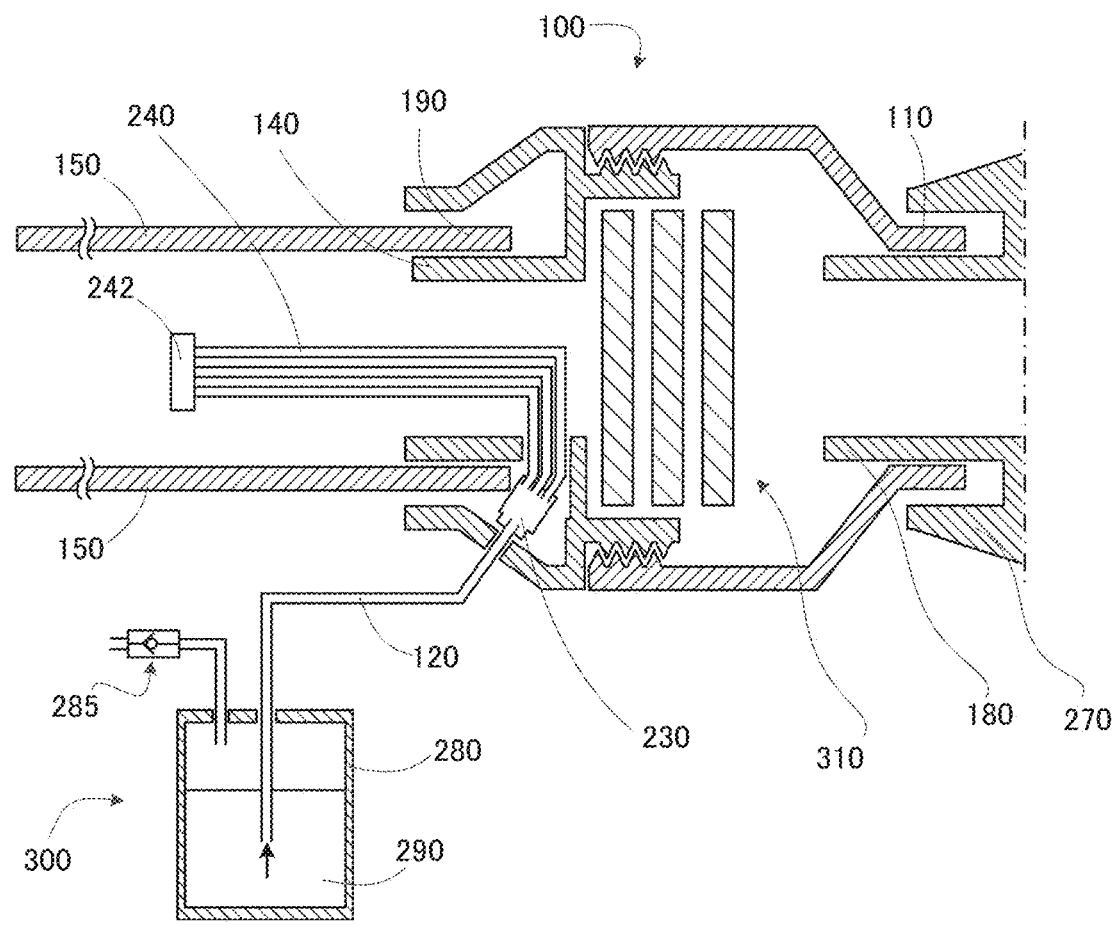
FIG. 5 is a cross-sectional view of a second embodiment of the silencer.
Figure 6:
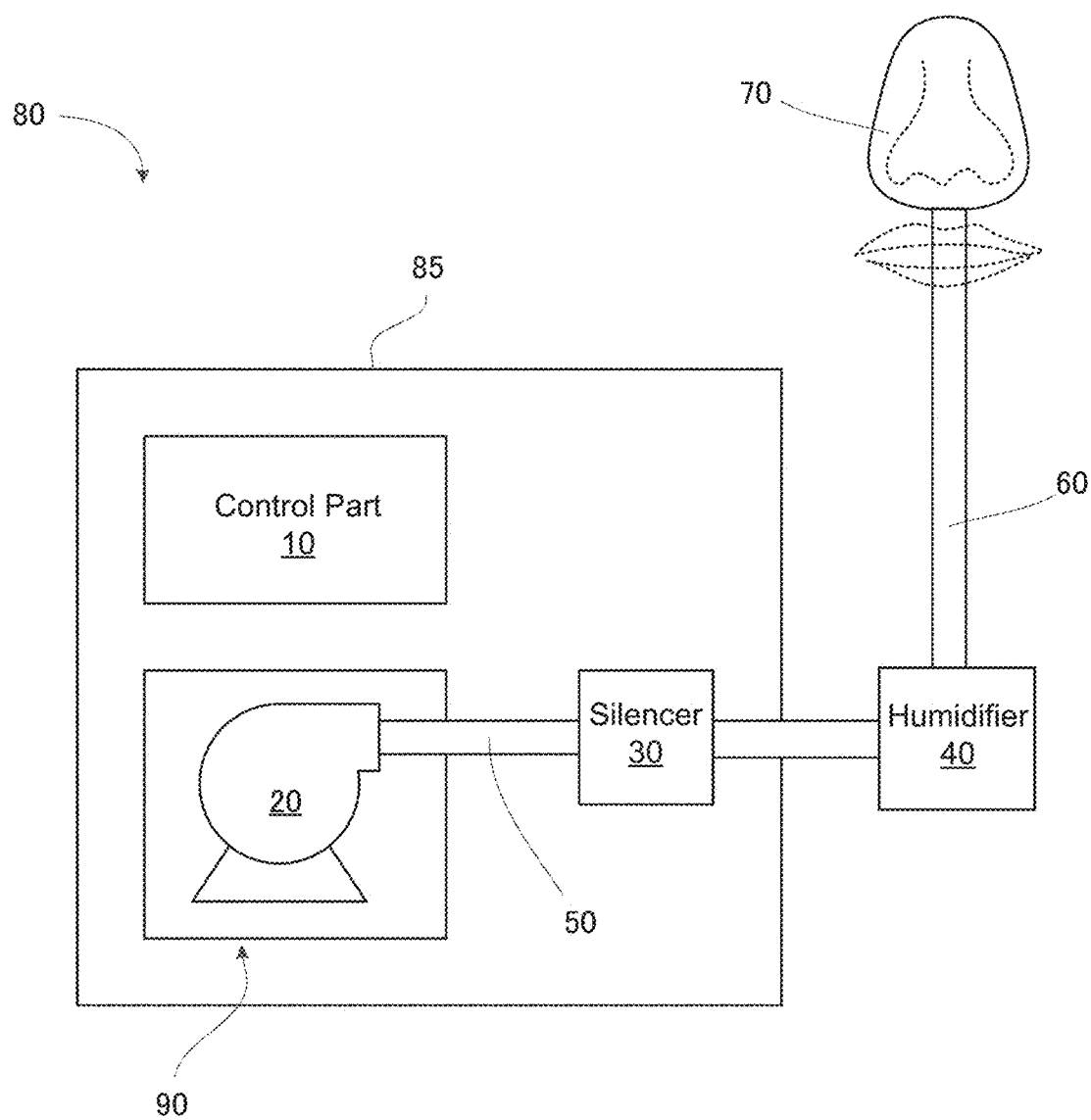
FIG. 6 is an explanatory view showing the configuration of a conventional respiratory assistance device.

FIG. 5 is an explanatory view of a second embodiment of the silencer. In the second embodiment, as shown in FIG. 5, filters 310 are disposed in an inner space of the silencer 100 instead of a silencing member having a through hole portion. The filters 310 have fine holes allowing pressurized air to thoroughly pass therethrough but insulating sound. With such a configuration, it is possible to acquire an advantageous effect of attenuating sound and, at the same time, acquire an advantageous effect of enhancing purity of pressurized air. In the case of the configuration shown in FIG. 5 where a plurality of filters 310 are provided, even when the fine holes per se formed in the filters 310 have a size which allows the fine hole to be visible by the naked eye, provided that the holes formed in the plurality of filters are not linearly aligned as viewed in the direction toward the second connection portion 140 from the first connection portion 110, it is possible to acquire an advantageous effect of insulating sound as a matter of course. When pressurized air is insulated by each filter, most of dust and dirt present in air impinge on and are adsorbed by the filter. The filters may be charged so as to cause the filters to adsorb dust and dirt thereon. The inside of the first housing member 220 and the second housing member 200 forming the silencer 100 may be covered by a member having a sound attenuation effect.

The present invention is not limited to the above-mentioned embodiments. For example, in the first embodiment, the first connection portion 110 has the female portion, and the second connection portion 140 has the male portion. However, it may be also considered that both the first connection portion 110 and the second connection portion 140 have an outer diameter substantially equal to an inner diameter of the air tube end portion 190 thus each having a connectable male portion. With such a configuration, the air tube can be connected to both ends of the silencer 100 and hence, it is possible to acquire an advantageous effect that the silencer 100 can be freely disposed in the air tube 150 at a position closer to the attachment part 70. With such a configuration, the silencer 100 becomes detachable irrespective of the blower device 170 so that ease of maintenance is further improved.

In the above-mentioned embodiments, the case is exemplified where the hollow fibers are used as the humidifying part 240. However, the present invention is not limited to such a case. For example, it may be considered a case where the silencing member 210 is caused to function as the humidifying part. To be more specific, a member which causes capillary action such as a non-woven fabric is made to pass through the water introduction passage 120, and is connected to the silencing member 210. In this configuration, sponge-like urethane foam or the like is used for forming the silencing member 210. With such a configuration, water sucked from the water storage part is evaporated from the silencing member 210 which functions as the humidifying part thus humidifying pressurized air. Such a configuration does not use hollow fibers leading to further simplification of the structure. Also in this case, by regularly replacing the silencing member 210, it is possible to prevent the occurrence of a sanitary problem.

In the above-mentioned embodiments of the present invention, the description has been made mainly with respect to the respiratory assistance device used for CPAP treatment. However, it is needless to say that the silencer according to the present invention is also applicable to a general artificial ventilator.

The silencer and the respiratory assistance device equipped with the silencer according to the present invention are not limited to the above-mentioned embodiments, and it is needless to say that various modifications are conceivable without departing from the gist of the present invention.

REFERENCE SIGNS LIST 1 control device
2 blower device
10 control part
20 blower
30 silencer
40 humidifier
50 flow passage
60 air tube
70 attachment part
80 respiratory assistance device
90 silencer box
100 silencer
110 first connection portion
120 water introduction passage
130 humidifier connection portion
140 second connection portion
150 air tube
160 electric power distribution line and communication means
170 blower device
180 breathing circuit connection port
190 air tube end portion
200 second housing member
210 silencing member
220 first housing member
230 connector
240 humidifying part
250 through hole portion
260 housing member connection portion
270 blower device casing end portion
280 water storage part
285 check valve
290 water
300 humidifier
310 filter

The invention claimed is:

1. Therapy equipment comprising:
a casing accommodating a blower for generating pressurized air;
an attachment part configured to be attached to a patient;
an air tube forming a flow passage between the casing and the attachment part; and a silencer inserted in the flow passage so as to reduce sound generated by the therapy equipment, wherein the silencer is provided outside the casing which accommodates the blower;

wherein the silencer includes:
   a housing part having an inner space;
   a first connection portion connectable to the casing; and
   a second connection portion connectable to the air tube;

the first connection portion having a female portion which has an inner diameter equal to an outer diameter of a breathing circuit connection port of the casing, the female portion being directly connectable to the breathing circuit connection port without going through any other tube, wherein when an inner circumference of the female portion comes into contact with the breathing circuit connection port, elasticity of the female portion generates a tightening force between the female portion and the breathing circuit connection port; and the second connection portion has a male portion which has an outer diameter equal to an inner diameter of an end portion of the air tube, the male portion being connectable to the air tube, the outer diameter of the male portion is equal to the outer diameter of the breathing circuit connection port of the casing, wherein when an inner circumference of the end portion of the air tube and an outer circumference of the male portion come into contact, elasticity of the air tube generates a tightening force between the end portion of the air tube and the male portion;

wherein the housing part is separable into a first housing member having the first connection portion, and a second housing member having the second connection portion;

further including a humidifier configured to humidify the pressurized air, wherein the silencer has a humidifier connection portion for connecting the silencer to the humidifier;

wherein the humidifier connection portion is provided to the second housing member;

the humidifier including:
   a water storage part configured to store water for humidification, which is located outside the silencer;
   a porous hollow fiber being disposed in the air tube; and
   a water introduction passage being located at the humidifier connection portion through which water is introduced from the water storage part to the hollow fiber.

2. The therapy equipment according to claim 1, wherein the housing part has a removable silencing member in the inner space, and the silencing member is disposed between the first connection portion and the second connection portion in the inner space of the housing part, and has at least one through hole portion through which the pressurized air is introduced from a blower side to an attachment part side.

3. The therapy equipment according to claim 1, wherein the housing part has a filter in the inner space, and the filter is disposed between the first connection portion and the second connection portion in the inner space of the housing part.

\* \* \* \* \*